(12) United States Patent
Owa

(10) Patent No.: US 10,416,128 B2
(45) Date of Patent: Sep. 17, 2019

(54) SUPERCRITICAL FLUID-LIQUID CHROMATOGRAPH, AND ANALYSIS METHOD THEREOF

(71) Applicant: SHIMADZU CORPORATION, Kyoto (JP)

(72) Inventor: Michiaki Owa, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 0 days.

(21) Appl. No.: 14/988,854

(22) Filed: Jan. 6, 2016

(65) Prior Publication Data

US 2016/0202218 A1    Jul. 14, 2016

(30) Foreign Application Priority Data

Jan. 14, 2015  (JP) ................................. 2015-005063

(51) Int. Cl.
*G01N 30/34* (2006.01)
*G01N 30/16* (2006.01)
(Continued)

(52) U.S. Cl.
CPC ............. *G01N 30/34* (2013.01); *B01D 15/40* (2013.01); *C07K 1/16* (2013.01); *G01N 30/16* (2013.01); *G01N 30/74* (2013.01); *Y02P 20/544* (2015.11)

(58) Field of Classification Search
CPC ........ G01N 30/32; G01N 30/34; G01N 30/16; G01N 30/74; G01N 30/02; G01N 30/88;
(Continued)

(56) References Cited

U.S. PATENT DOCUMENTS 7,670,487 B2 *   3/2010   Wikfors ............... B01D 15/163
                                                       210/137
8,992,778 B2 *   3/2015   Liu ........................ G01N 30/34
                                                       210/101
(Continued)

FOREIGN PATENT DOCUMENTS

CN         103512987 A        1/2014
EP         2 677 313 A1      12/2013
(Continued)

OTHER PUBLICATIONS

Multidimensional Chromatography: Techniques and Applications (Chromatographic Science Series), edited by Hernan J. Cortes, CRC Press, 1 edition, pp. 338-341.*
(Continued)

*Primary Examiner* — Peter J Macchiarolo
*Assistant Examiner* — Irving A Campbell
(74) *Attorney, Agent, or Firm* — Westerman, Hattori, Daniels & Adrian, LLP

(57) ABSTRACT

A back pressure valve configured to switch between a pressurized state and a released state open to an atmosphere is used as a back pressure valve in a supercritical fluid chromatograph. Switching from a state of supercritical fluid chromatography analysis to liquid chromatography is performed by stopping a pump that supplies a supercritical fluid, continuously operating a pump that supplies a solvent used as a modifier, and bringing the back pressure valve into the released state.

6 Claims, 6 Drawing Sheets

(51) Int. Cl.
*G01N 30/74* (2006.01)
*B01D 15/40* (2006.01)
*C07K 1/16* (2006.01)

(58) Field of Classification Search
CPC ........ B01D 15/40; B01D 15/08; B01D 15/16; B01D 15/166; Y02P 20/544; C07K 1/16
USPC .............................................. 73/61.55, 61.56
See application file for complete search history.

(56) References Cited

U.S. PATENT DOCUMENTS

2004/0018099 A1* 1/2004 Berger .................. G01N 30/32
  417/313
2013/0048095 A1* 2/2013 Wikfors .............. F04B 11/0075
  137/7

FOREIGN PATENT DOCUMENTS

JP        2006-52968 A    2/2006
WO        2013/062635 A2  5/2013

OTHER PUBLICATIONS

Office Action dated Jul. 3, 2017, issued in counterpart Chinese Application No. 201510759432.5, with English translation. (15 pages).

Office Action dated Feb. 14, 2018, issued in counterpart Chinese Application No. 201510759432.5, with English translation. (10 pages).

Office Action dated May 15, 2018, issued in counterpart Japanese Application No. 2015-005063, with English machine translation. (6 pages).

Notice of Decision for Final Rejection dated Mar. 11, 2019, issued in counterpart CN Application No. 201510759432.5, with English machine translation. (13 pages).

Office Action dated Aug. 31, 2018, issued in counterpart Chinese Application No. 201510759432.5, with English translation. (16 pages).

* cited by examiner

SUPERCRITICAL FLUID-LIQUID CHROMATOGRAPH, AND ANALYSIS METHOD THEREOF

BACKGROUND OF THE INVENTION

1. Field of the Invention

The present invention relates to supercritical fluid chromatography (SFC) that uses a supercritical fluid as a mobile phase.

2. Description of the Related Art

In recent years, along with technological innovations such as sensitivity improvement in mass spectrometers and other such detectors, along with improvement in selectivity of molecules at the time of detection, exhaustive quantitative analysis of small molecule compounds (compounds having molecular weight of about 1000 or less) has been possible by joining various types of chromatography and a detector. For example, in metabolomics research that is omics science based on all metabolites in a living body, complex phenotypes in microorganisms, plants, animals, or food samples can be analyzed quantitatively with high resolution. For this reason, the exhaustive quantitative analysis does not only contribute to basic science research, but has also started to be used as a powerful analysis tool in practical industrial research such as support for drug development, toxicity evaluation, and food function analysis. Moreover, the exhaustive quantitative analysis has been essential technology in the field of pesticide residue tests or drug residue tests.

Generally, since small molecule compounds have diverse physicochemical properties, various kinds of separation technology are necessary for comprehensive measurement of such compounds.

In SFC, a supercritical fluid is used for the mobile phase (see JP 2006-52968 A). The supercritical fluid is a substance in a state above a critical temperature and a critical pressure, and has nature favorable for chromatography such as low viscosity and high diffusivity. SFC maintains high separation ability even in high flow velocity analysis, and has a potential of being capable of selecting a wide range of separation modes by adding a polar solvent (modifier) or by changing a temperature or a back pressure. Carbon dioxide, which is generally used in SFC, has a critical pressure of 7.38 MPa and a critical temperature of 31.1° C. that is relatively close to normal temperature, is non-flammable and chemically unreactive, and very pure carbon dioxide is available at a low cost. For this reason, carbon dioxide is most often used in SFC. Supercritical carbon dioxide ($SCCO_2$) has a physical property of low polarity close to hexane, and the polarity of the mobile phase can be changed significantly by adding a polar organic solvent such as methanol as a modifier. Accordingly, heretofore, SFC has been applied as a separation analysis technique useful for fast separation analysis of lipids that represent hydrophobic metabolites.

On the other hand, liquid chromatography (LC) is commonly used for analysis of metabolites, and it can be said that LC is the most widely used chromatography method. However, LC has different measurement conditions depending on measurement targets, and cannot simultaneously separate a wide range of metabolites by one liquid chromatograph.

SUMMARY OF THE INVENTION

Since supercritical fluid chromatography and liquid chromatography each have suitable analysis target compounds, a combination of both analysis methods can cover a wide range of compounds.

Thus, it is convenient that supercritical fluid chromatography and liquid chromatography can be executed by one analysis device. For example, a case of switching from supercritical fluid chromatography to liquid chromatography in one analysis device will be considered. During analysis in the supercritical fluid chromatography, a back pressure is applied to keep the mobile phase in a supercritical fluid state. In the case where, during the analysis, an addition amount of an organic solvent that is a modifier is set to increase so that the mobile phase only contains the organic solvent, this means switching to liquid chromatography by means of the organic solvent. However, since viscosity of the mobile phase increases as the addition amount of the modifier increases, a pressure applied to a delivery pump, a column, or a cell of a detector increases. Along with the increase of the pressure, a withstanding pressure of the delivery pump, the column, or the detector cell is exceeded, and the exceeding withstanding pressure is likely to cause seal leakage of the delivery pump or decrease in durability of the column or the detector cell. That is, it can be understood that switching of the analysis mode from supercritical fluid chromatography to liquid chromatography using only the modifier cannot be easily achieved by extension of supercritical fluid chromatography using a current supercritical fluid chromatograph.

An object of the present invention is to realize a device and method that enables supercritical fluid chromatography and liquid chromatography to be executed by one analysis device in spite of the above-described problem.

A supercritical fluid-liquid chromatograph of the present invention includes: a first solvent delivery section that delivers a solvent to be a supercritical fluid by a first pump; a second solvent delivery section that delivers an organic solvent having polarity and compatibility with the solvent by a second pump; a separation column that is arranged on an analysis channel downstream a merging section of the first solvent delivery section and the second solvent delivery section; a sample injection section that is arranged between the merging section and the separation column in the analysis channel and injects a sample into the analysis channel; a back pressure valve that is arranged downstream the separation column with respect to flow of a mobile phase in the analysis channel and is capable of keeping an inside of the analysis channel at a pressurized state to maintain the mobile phase in a supercritical fluid state; a detector that is arranged between the separation column and the back pressure valve in the analysis channel and/or outside a release port of the back pressure valve to an atmosphere and detects a sample component eluted from the separation column; and a control section that controls operations of the first pump, the second pump, and the back pressure valve.

The back pressure valve is then configured to switch between the pressurized state and a released state open to the atmosphere, and the control section is configured to perform switching from supercritical fluid chromatography where the first pump and the second pump are brought into an operating state and the back pressure valve is maintained for the pressurized state, to liquid chromatography where the first pump is stopped, the second pump continues to operate, and the back pressure valve is brought into the released state.

An analysis method of the present invention uses an analysis device including an analysis channel provided with a separation column, a mobile phase delivery section that supplies a mobile phase to the analysis channel, a sample injection section that injects a sample between the separation column and the mobile phase delivery section in the analysis channel, a back pressure valve that is arranged downstream the separation column with respect to flow of a mobile phase in the analysis channel and is capable of keeping an inside of the analysis channel at a pressurized state to maintain the mobile phase in a supercritical fluid state, and a detector that is arranged between the separation column and the back pressure valve in the analysis channel and/or outside a release port of the back pressure valve to an atmosphere and detects a sample component eluted from the separation column, and the method includes the following (A) to (C).

(A) Supplying a mobile phase to be in a supercritical fluid state as the mobile phase from the mobile phase delivery section, injecting a sample from the sample injection section while maintaining the mobile phase in the analysis channel in the supercritical fluid state by the back pressure valve, and starting supercritical fluid chromatography analysis, (B) after the supercritical fluid chromatography analysis where the mobile phase is a mixed solution of a solvent to be a supercritical fluid and an organic solvent having polarity and compatibility with the solvent, switch from a state of supercritical fluid chromatography to a state of liquid chromatography by switching the mobile phase supplied from the mobile phase delivery section so as to contain only the organic solvent and releasing the back pressure valve to an atmospheric pressure, and (C) subsequently performing liquid chromatography analysis using the mobile phase containing the organic solvent.

According to the present invention, a back pressure valve configured to switch between a pressurized state and a released state open to an atmosphere is used as a back pressure valve in a supercritical fluid chromatograph, and switching from the state of supercritical fluid chromatography analysis to liquid chromatography is performed by stopping a pump that supplies a supercritical fluid, and by continuously operating a pump that supplies a solvent used as a modifier. For this reason, supercritical fluid chromatography and liquid chromatography can be executed by one analysis device.

Figure 3:
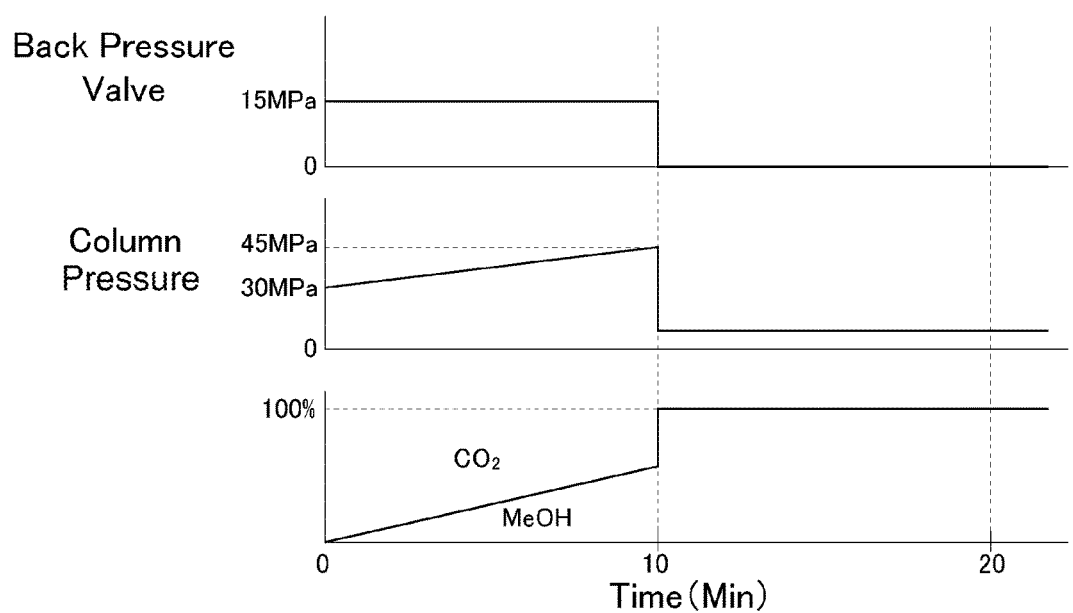
Figure 4:
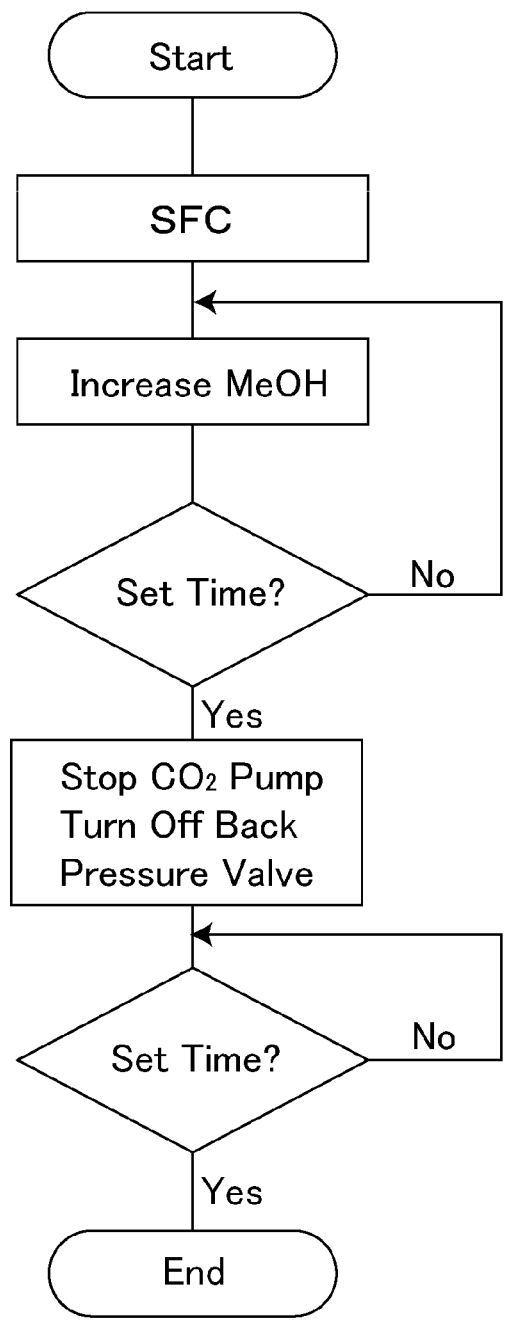
Figure 5A:
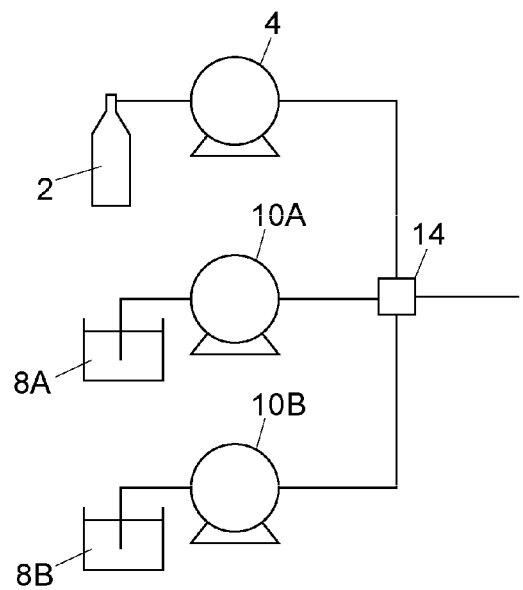
Figure 5B:
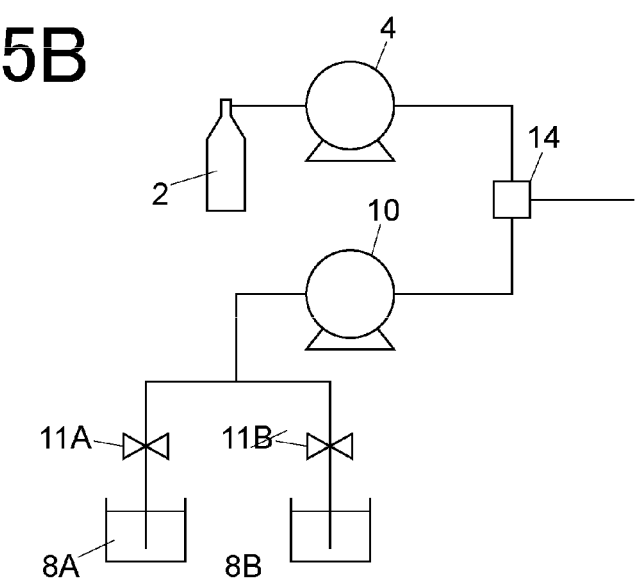
Figure 6:
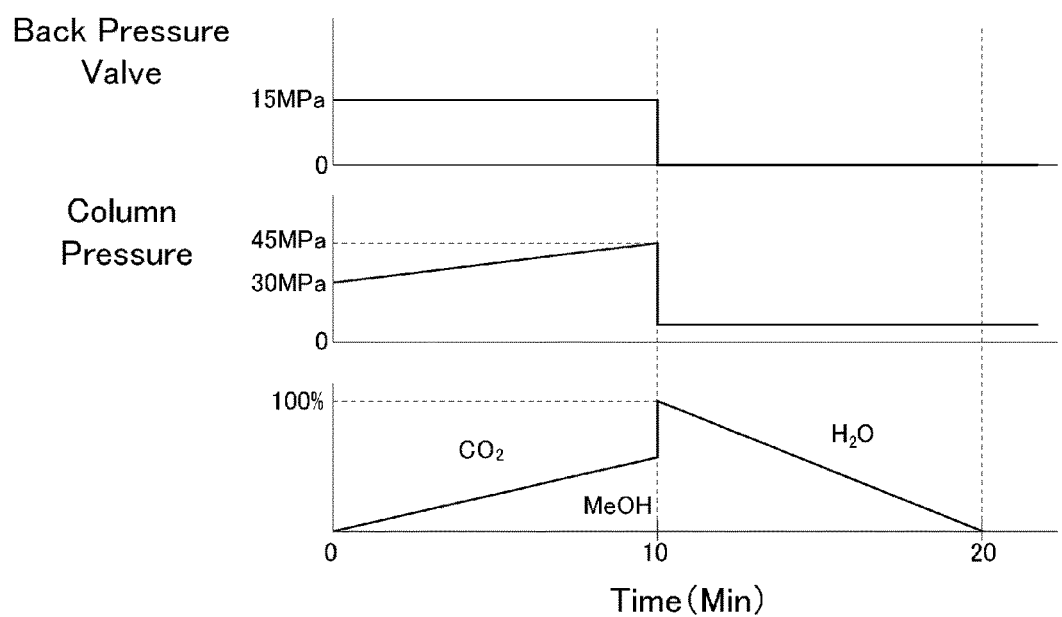

A view showing a chromatogram according to the example;

FIG. 3 is a time chart showing an example of an operation according to the example;

FIG. 4 is a flow chart showing the operation;

FIG. 5A is a channel view showing a mobile phase delivery section according to another example;

FIG. 5B is a channel view showing a mobile phase delivery section according to further another example; and FIG. 6 is a time chart showing an example of an operation according to the examples in FIGS. 5A and 5B.

DETAILED DESCRIPTION OF THE INVENTION

According to an embodiment, a control section includes an analysis program storage section that stores an analysis program of setting operation conditions of a first pump, a second pump, and a back pressure valve with respect to time. Hence, the control section is configured to execute switching from supercritical fluid chromatography to liquid chromatography, based on the analysis program.

In another embodiment, a third solvent delivery section that supplies a third solvent capable of constituting together with an organic solvent to be a modifier a mobile phase for the liquid chromatography by a third pump is connected to a merging section. Then, the analysis program storage section of the control section also stores an analysis program for gradient analysis in the liquid chromatography, and the control section is configured to control the second pump and the third pump to perform gradient analysis in the liquid chromatography.

According to further another embodiment, a second solvent delivery section is configured to be capable of supplying, in addition to the organic solvent to be the modifier, the third solvent capable of constituting together with the organic solvent the mobile phase for the liquid chromatography by the second pump. Then, the analysis program storage section of the control section also stores the analysis program for the gradient analysis in the liquid chromatography, and the control section is configured to control an operation of the second solvent delivery section to supply, in the supercritical fluid chromatography, only the organic solvent to be the modifier from the second solvent delivery section, and to supply, in the liquid chromatography, the organic solvent and the third solvent from the second solvent delivery section and perform gradient analysis.

According to an embodiment of an analysis method, (C) is gradient analysis where another solvent is mixed with the organic solvent as the mobile phase.

Figure 1:
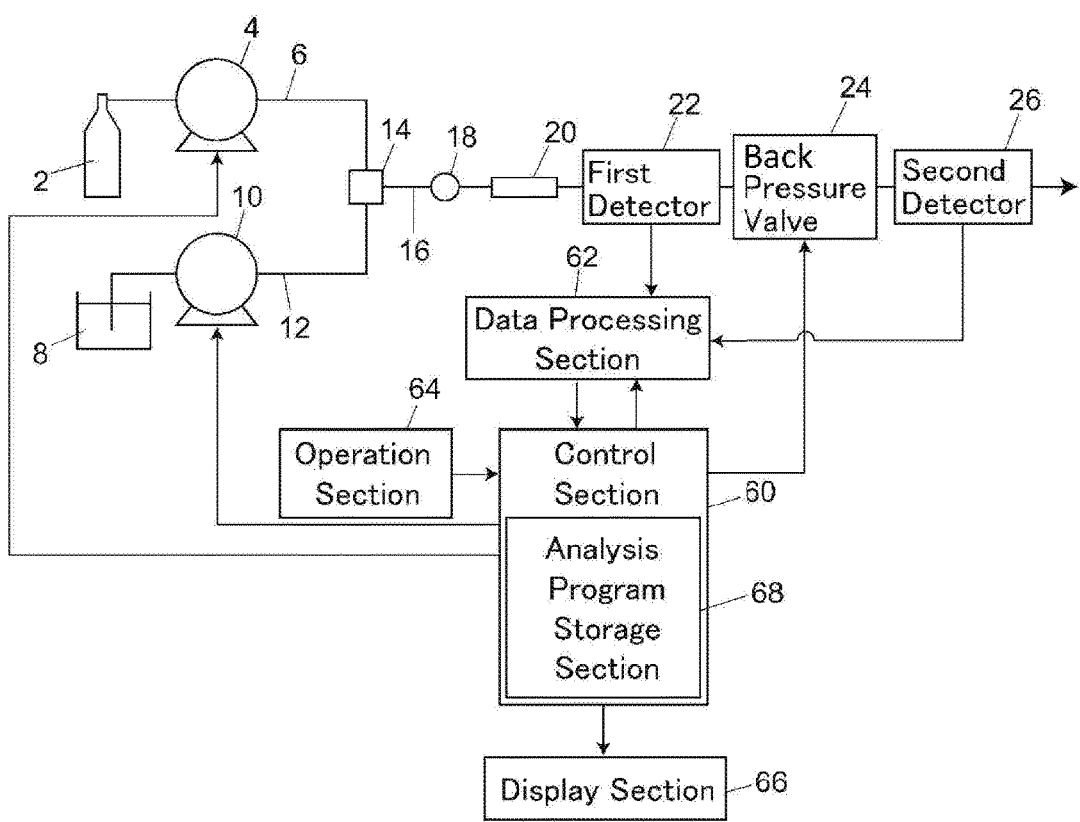
FIG. 1 is a schematic configuration view showing a supercritical fluid chromatography-liquid chromatography analysis device according to an example.

An example of a supercritical fluid-liquid chromatograph is shown in FIG. 1. In order to supply the mobile phase, the supercritical fluid-liquid chromatograph is provided with a first solvent delivery section that delivers a supercritical fluid contained in a tank 2 by a first pump (SFC pump) 4, and the second solvent delivery section that delivers a modifier solution 8 by a second pump (modifier pump) 10. A delivery channel 6 of the first solvent delivery section and a delivery channel 12 of the second solvent delivery section are connected to a mixer 14 arranged at the merging section.

A channel through which the mobile phase is sent from the mixer 14 is an analysis channel 16. A sample injection section 18 that injects a sample into the analysis channel 16, a separation column 20, a first detector 22, a back pressure valve 24, and a second detector 26 are arranged on the analysis channel 16 from the upstream side with respect to flow of the mobile phase. The separation column 20 is accommodated inside a column oven (not shown), and is kept at a constant temperature.

As the supercritical fluid, for example, carbon dioxide in a liquid state can be used, and methanol or a methanol solution can be used as the modifier. The sample injection section 18 is, for example, an autosampler.

The back pressure valve 24 can keep the inside of the analysis channel 16 at a constant pressure (pressurized state) in order to maintain the mobile phase inside the analysis channel 16 in the supercritical fluid state when the mobile phase can be in the supercritical fluid state. Moreover, the back pressure valve 24 is configured to switch between the pressurized state and a released state open to an atmosphere.

An ultraviolet-visible absorption spectrophotometer, for example, is used as the first detector 2 that is arranged between the separation column 20 and the back pressure valve 24. The sample that is introduced from the sample injection section 18 into the analysis channel 16 is separated at the separation column 20, and is converted into an electrical signal at the detector 22.

As the second detector 26 that is arranged on the downstream side of the back pressure valve 24, a detector requiring removal of the mobile phase, such as a mass spectrometer or an ELSD (Evaporated Light Scattering Detector), is used. The mobile phase is in the supercritical fluid state or the liquid state inside the analysis channel 16 on the upstream side of the back pressure valve 24. However, since the mobile phase is discharged at an atmospheric pressure on the downstream side of the back pressure valve 24, sample components separated at the separation column 20 and eluted become in the form of a mist together with the mobile phase on the downstream side of the back pressure valve 24 to be discharged.

In the case of using a mass spectrometer as the detector 26, the eluted sample components are ionized by application of a voltage (electro-spray voltage) between a discharge port for the mobile phase downstream the back pressure valve 24 and an ionization chamber of the mass spectrometer, and analyzed by the mass spectrometer.

Both the detectors 22 and 26 may be provided, but only one of the detectors may be provided depending on application. For example, in the case of only performing analysis, any one of the detectors 22 and 26 may be provided. Moreover, for example, in the case of performing fractionation, only the detector 22 is provided.

A control section 60 is provided for controlling operations of the first pump 4, the second pump 10, and the back pressure valve 24. The control section 60 is configured to perform the switching from the supercritical fluid chromatography where the first pump 4 and the second pump 10 are brought into the operating state and the back pressure valve 24 is maintained in the pressurized state, to the liquid chromatography where the first pump 4 is stopped, the second pump 10 continues to operate, and the back pressure valve 24 is brought into the released state.

A data processing section 62 is connected to the control section 60. The data processing section 62 takes in detection signals of the detectors 22 and 26, and creates a chromatogram or a mass spectrogram together with the control section 60. An operation section 64 such as a keyboard that inputs analysis conditions or the like, and a display section 66 such as a liquid crystal display that displays a chromatogram or a mass spectrogram of an analysis result are further connected to the control section 60.

As an example, the control section 60 includes an analysis program storage section 68 that stores the analysis program of setting the operation conditions of the first pump 4, the second pump 10, and the back pressure valve 24 with respect to time, and is configured to execute the switching from the supercritical fluid chromatography to the liquid chromatography based on the analysis program.

The control section 60 and the data processing section 62 are a computer, and may be a computer dedicated to the supercritical fluid-liquid chromatograph, or may be a general-purpose personal computer. The control section 60 and the data processing section 62 may be realized by a common computer, or by separate computers.

An example of the back pressure valve 24 is shown in FIGS. 2A to 2D. However, the back pressure valve 24 is not limited to the one shown in FIGS. 2A to 2D, and may adopt another structure as long as the valve can keep the inside of the analysis channel 16 at a constant pressure and can switch between its pressurized state and its released state.

The back pressure valve 24 shown in FIGS. 2A to 2D is provided with pipe connection sections 31 and 32 for connecting pipes to facing side surfaces of a pressure control block 30. The pipe connection sections 31 and 32 are connected to each other by one internal channel 40 provided inside the pressure control block 30. A material of the pressure control block 30 is a material having excellent chemical-resistance and an excellent pressure withstanding property, such as a stainless steel (SUS316). An inner diameter of the internal channel 40 is, for example, about 0.1 to 0.3 mm.

A pipe 33 constituting a part of the analysis channel 16 is inserted in the pipe connection section 31 and is fixed by a male nut 34, and a pipe 36 is inserted in the pipe connection section 32 and is fixed by a male nut 38. The pipe 33 is an inlet channel into the internal channel 40 constituting a pressure control chamber, and the pipe 36 is an outlet channel. The mobile phase enters the internal channel 40 through the pipe 33, and is discharged outside through the pipe 36.

Figure 2A:
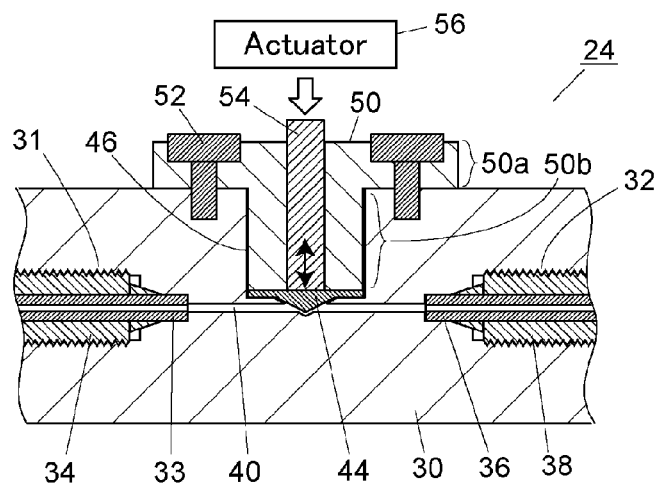
FIG. 2A is a sectional view showing an example of a pressure control valve used as a back pressure valve in the example.
Figure 2B:
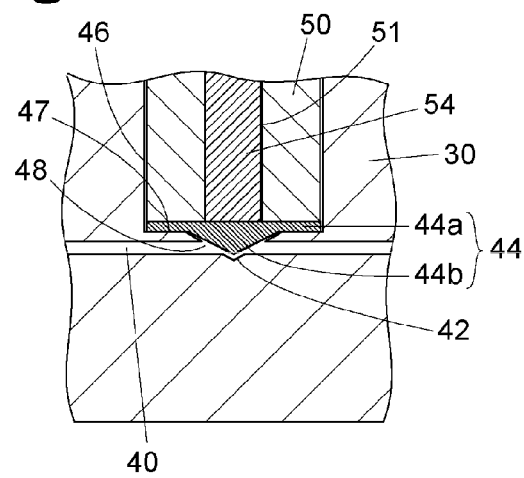
FIG. 2B is a sectional view showing a valve mechanism portion of the pressure control valve in an enlarged manner.
Figure 2C:
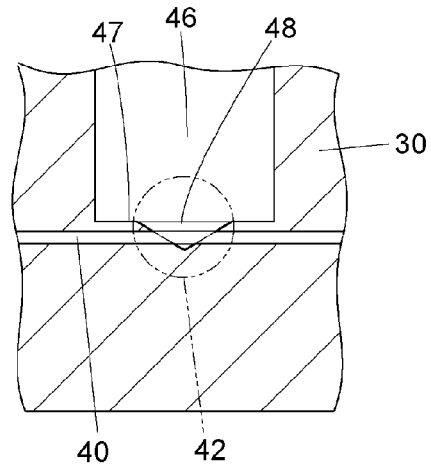
FIG. 2C is a sectional view showing a shape of a recessed section of the pressure control valve in a state where a disc member and a pressing member are removed.
Figure 2D:
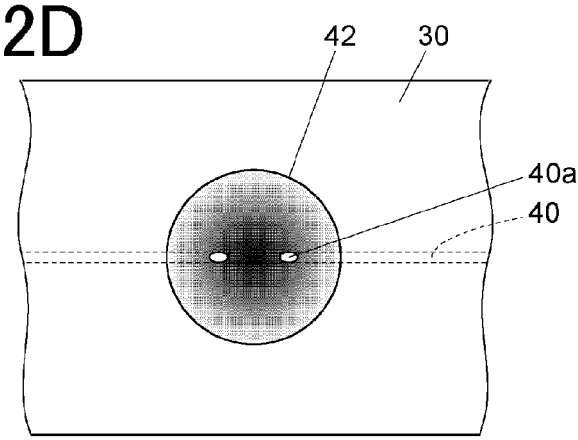
FIG. 2D is a view showing from above the inside of the recessed section of the pressure control valve.

The pressure control block 30 is provided with a carved hole 46 that is carved in the direction orthogonal to the extending direction of the internal channel 40, at a position above the internal channel 40. A bottom surface of the carved hole 46 reaches near the internal channel 40. A recessed section 42 is formed at a bottom surface 47 (recessed section-formed surface) of the carved hole 46. The recessed section 42 is formed in a cone shape that is tapered from its opening 48 toward its bottom portion. The recessed section 42 crosses the internal channel 40, and cuts off the internal channel 40 into two channels. As shown in FIG. 2D, when the inside of the recessed section 42 is seen from above the opening 48, two end portions 40a of the channel 40 cut by the recessed section 42 are seen inside the recessed section 42. Note that the shape of the recessed section 42 is not limited to the cone shape, and may be in a shape that is tapered toward the bottom portion.

A disc member 44 is arranged at the bottom portion of the carved hole 46. The disc member 44 includes a circular sealing portion 44a having a planar shape that has about the same size as the planar shape of the carved hole 46, and a protruding portion 44b in a shape protruding from a center portion of one plane of the sealing portion 44a so as to be fitted in the recessed section 42. Here, a surface on the protruding portion 44b side of the disc member 44 will be referred to as a front surface, and a surface on the opposite side to the front surface will be referred to as a back surface. The front surface of the disc member 44 is faced toward the recessed section 42 side, and the protruding portion 44b is fitted in the recessed section 42. A surface of the sealing portion 44a that surrounds the protruding portion 44b is in close contact with the bottom surface 47 of the carved hole 46, and seals the opening 48.

A pressing member 50 that presses the disc member 44 against the bottom surface 47 of the carved hole 46 is attached to the pressure control block 30 by screws 52. The pressing member 50 includes a circular flange portion 50a having a planar shape larger than the carved hole 46, and a columnar tip end portion 50b that protrudes from a center portion of one plane of the flange portion 50a so as to be fitted in the carved hole 46. The tip end portion 50b is inserted in the carved hole 46, and a peripheral portion of the flange portion 50a is fixed to the pressure control block 30 by the screws 52. A tip end surface of the tip end portion 50b is in contact with the back surface of the disc member 44, and force of pressing the disc member 44 against the bottom surface 47 side of the carved hole 46 is adjusted by the degree of fastening of the screws 52.

A through hole 51 penetrating the flange portion 50a and the tip end portion 50b is provided at a center portion of the pressing member 50. A columnar pressing rod 54 penetrates the inside of the through hole 51, and a tip end of the pressing rod 54 is in contact with a center portion of the back surface of the disc member 44. The pressing rod 54 is driven in one direction (vertical direction in the figure) by an actuator 56 such as a piezo actuator. The drive of the pressing rod 54 by the actuator 56 causes a tip end surface of the pressing rod 54 to press and deform the disc member 44, and the deformation of the disc member 44 displaces the protruding portion 44b inside the recessed section 42. The displacement of the protruding portion 44b inside the recessed section 42 adjusts the size of a gap between the recessed section 42 and the protruding portion 44b, and the adjustment of the size of the gap adjusts the size of the opening area where one end of the internal channel 40 communicates with the other end of the internal channel 40.

When supercritical fluid chromatography analysis is executed, the back pressure valve 24 shown in FIGS. 2A to 2D pushes the pressing rod 54 by the actuator 56 to adjust the size of the gap between the recessed section 42 and the protruding portion 44b such that a predetermined pressure is applied, and brings the mobile phase into the supercritical fluid state. When the supercritical fluid chromatography is switched to the liquid chromatography, release of the pressing of the pressing rod 54 by the actuator 56 increases the opening area where one end of the internal channel 40 communicates with the other end of the internal channel 40, and the back pressure valve 24 is opened to the atmospheric pressure.

Next, an example of supercritical fluid chromatography-liquid chromatography analysis using the device according to this example will be described with reference to FIGS. 3 and 4.

(1) Analysis is started with the supercritical fluid chromatography. Therefore, the pump 4 of the first solvent delivery section is operated in a state where the pump 10 of the second solvent delivery section is stopped, and only liquid carbon dioxide is supplied as the mobile phase, and the sample is injected from the sample injection section 18. The back pressure valve 24 is set in such a way that a pressure of, for example, 15 MPa is applied to the back pressure valve 24.

(2) Operation of the pump 10 of the second solvent delivery section is started after the analysis is started, and for example, methanol is supplied as the modifier. The operations of the pumps 4 and 10 are controlled in such a way that the proportion of the methanol to the liquid carbon dioxide gradually increases as shown in FIG. 3 while the total flow rate of the liquid carbon dioxide and the methanol is kept at a predetermined constant flow rate. The control is performed in such a way that the proportion to the methanol becomes, for example, 50% after set time (for example, 10 minutes) have passed from the start of the analysis. At this time, since the viscosity of the mobile phase increases as the proportion of the methanol in the liquid carbon dioxide increases, the pressure at the separation column 20 rises.

(3) After the set time, the pump 4 of the first solvent delivery section is stopped. The pump 10 of the second solvent delivery section sets the flow rate of the methanol to a predetermined constant flow rate. Meanwhile, pressure setting of the back pressure valve 24 is released and the back pressure valve 24 is opened to the atmospheric pressure.

Subsequently, liquid chromatography analysis using the methanol as the mobile phase is continued for predetermined time (for example, 20 minutes).

The control section 60 executes the above-described operation, based on the analysis program stored in the analysis program storage section 68 of the control section 60.

The gradient analysis where the proportion of the methanol that is the modifier in the supercritical fluid chromatography is set to gradually increase with time is performed in the above-described example, but the proportion of the modifier may be set to increase stepwise, or may be set to be always constant proportion.

Moreover, the liquid chromatography analysis using the mobile phase of uniform composition is performed in the above-described example, but the liquid chromatography may be gradient analysis. Such examples are shown in FIGS. 5A and 5B. FIG. 5A shows a case of high-pressure gradient, and FIG. 5B shows a case of low-pressure gradient.

In the high-pressure gradient in FIG. 5A, for example, methanol 8A and water 8B are prepared as solvents constituting a mobile phase for liquid chromatography. The methanol 8A is used as a modifier in supercritical fluid chromatography and is supplied by a pump 10A. The water 8B is supplied by a pump 10B, and the methanol 8A and the water 8B are mixed by a mixer 14 so as to be the mobile phase. The ratio between the methanol 8A and the water 8B is adjusted based on flow rates of the respective pumps 10A and 10B.

Also in the case of the low-pressure gradient in FIG. 5B, as an example, methanol 8A and water 8B are prepared as solvents constituting a mobile phase for liquid chromatography. The ratio between the methanol 8A and the water 8B is adjusted by on/off operations of respective on/off valves arranged between a pump 10 and the methanol 8A and the water 8B.

An example of a supercritical fluid chromatography-liquid chromatography analysis according to this example is shown in FIG. 6. An operation of the supercritical fluid chromatography analysis is the same as that shown in FIGS. 3 and 4.

The liquid chromatography following the supercritical fluid chromatography analysis is gradient where the mobile phase is 100 percent methanol at first and the proportion of water gradually increases.

Also in this example, the control section 60 executes the operation, based on the analysis program stored in the analysis program storage section 68 of the control section 60.

The proportion of the mobile phase, the set pressure of the back pressure valve 24, the time for switching from the supercritical fluid chromatography to the liquid chromatography, and the like described in the examples are described as an example, and the present invention is not limited to these examples.

It is preferable to pass the solvent to be used as the mobile phase for the liquid chromatograph through a degasifier and remove gas in the solvent before the solvent is suctioned in by the pump.

What is claimed is:

1. A supercritical fluid-liquid chromatograph comprising:
   a first solvent delivery section for delivering a solvent to be a supercritical fluid by a first pump;

a second solvent delivery section for delivering an organic solvent having polarity and compatibility with the solvent by a second pump;

a separation column arranged on an analysis channel downstream a merging section of the first solvent delivery section and the second solvent delivery section;

a sample injection section arranged between the merging section and the separation column in the analysis channel, for injecting a sample into the analysis channel;

a back pressure valve arranged downstream the separation column with respect to flow of a mobile phase in the analysis channel, capable of keeping an inside of the analysis channel at a pressurized state to maintain the mobile phase in a supercritical fluid state;

a detector arranged between the separation column and the back pressure valve in the analysis channel and/or outside a release port of the back pressure valve to an atmosphere, for detecting a sample component eluted from the separation column; and a control section for controlling operations of the first pump, the second pump, and the back pressure valve, wherein the back pressure valve is configured to switch between the pressurized state and a released state open to the atmosphere, wherein the control section is configured to perform switching, at a predetermined timing during the execution of an analysis of the sample, from a state for performing supercritical fluid chromatography analysis where the first pump and the second pump are brought into an operating state and the back pressure valve is maintained for the pressurized state, to a state for performing liquid chromatography analysis where the first pump is stopped, the second pump continues to operate, and the back pressure valve is brought into the released state, and wherein the first solvent delivery section and the back pressure valve are connected to the analysis channel in both of the state for performing supercritical fluid chromatography analysis and the state for performing liquid chromatography analysis.

2. The supercritical fluid-liquid chromatograph according to claim 1, wherein the control section includes an analysis program storage section for storing an analysis program of setting operation conditions of the first pump, the second pump, and the back pressure valve with respect to time, and wherein the supercritical fluid-liquid chromatograph executes the switching from the state for performing supercritical fluid chromatography analysis to the state for performing liquid chromatography analysis, based on the analysis program.

3. The supercritical fluid-liquid chromatograph according to claim 2, wherein a third solvent delivery section for supplying a third solvent capable of constituting together with the organic solvent the mobile phase for the liquid chromatography by a third pump is connected to the merging section, wherein the analysis program storage section also stores an analysis program for gradient analysis in the liquid chromatography analysis, and wherein the control section is configured to control the second pump and the third pump to perform gradient analysis in the liquid chromatography analysis.

4. The supercritical fluid-liquid chromatograph according to claim 2, wherein the second solvent delivery section is configured to be capable of supplying, in addition to the organic solvent, a third solvent is configured to be capable of constituting together with the organic solvent the mobile phase for the liquid chromatography by the second pump, wherein the analysis program storage section also stores the analysis program for the gradient analysis in the liquid chromatography, and wherein the control section is configured to control an operation of the second solvent delivery section to supply, in the state for performing supercritical fluid chromatography analysis, only the organic solvent from the second solvent delivery section, and to supply, in the state for performing liquid chromatography analysis, the organic solvent and the third solvent from the second solvent delivery section and perform gradient analysis in the liquid chromatography analysis.

5. An analysis method that uses an analysis device including an analysis channel provided with a separation column, a mobile phase delivery section comprising a first pump for delivering a solvent to be a supercritical fluid and a second pump for delivering an organic solvent having polarity and compatibility with the solvent, for supplying a mobile phase to the analysis channel, a sample injection section for injecting a sample between the separation column and the mobile phase delivery section in the analysis channel, a back pressure valve arranged downstream of the separation column with respect to flow of a mobile phase in the analysis channel, capable of keeping an inside of the analysis channel at a pressurized state to maintain the solvent in a supercritical fluid state, and a detector arranged between the separation column and the back pressure valve in the analysis channel and/or outside a release port of the back pressure valve to an atmosphere, for detecting a sample component eluted from the separation column, the method comprising:

(A) supplying a mobile phase including the solvent to be in a supercritical fluid state as the mobile phase from the mobile phase delivery section, injecting a sample from the sample injection section while maintaining the mobile phase in the analysis channel in the supercritical fluid state by the back pressure valve, and starting supercritical fluid chromatography analysis;

(B) after the supercritical fluid chromatography analysis where the mobile phase is a mixed solution of the solvent and the organic solvent, switching, at a predetermined timing during the execution of an analysis of the sample, from a state for performing supercritical fluid chromatography analysis to a state for performing liquid chromatography analysis by switching the mobile phase supplied from the mobile phase delivery section so as to contain only the organic solvent and releasing the back pressure valve to an atmospheric pressure, and (C) subsequently performing liquid chromatography analysis using the mobile phase containing the organic solvent, wherein the switching from the state for performing supercritical fluid chromatography analysis to the state for performing liquid chromatography analysis is performed by the first pump being stopped while the first pump is connected to the analysis channel.

6. The analysis method according to claim 5, wherein the step (C) is gradient analysis where another solvent is mixed with the organic solvent as the mobile phase.

\* \* \* \* \*